United States Patent
Toppi

(10) Patent No.: US 10,603,145 B1
(45) Date of Patent: Mar. 31, 2020

(54) DENTAL DEVICE FOR APPLYING MEDICINE TO A PATIENT'S TOOTH

(71) Applicant: David Toppi, San Diego, CA (US)

(72) Inventor: David Toppi, San Diego, CA (US)

( * ) Notice: Subject to any disclaimer, the term of this patent is extended or adjusted under 35 U.S.C. 154(b) by 0 days.

(21) Appl. No.: 16/589,885

(22) Filed: Oct. 1, 2019

(51) Int. Cl.
| | |
|---|---|
| *A61C 17/02* | (2006.01) |
| *A61C 15/04* | (2006.01) |
| *A61C 17/08* | (2006.01) |
| *A61C 17/06* | (2006.01) |
| *A61Q 11/00* | (2006.01) |
| *A61K 8/21* | (2006.01) |

(52) U.S. Cl.
CPC ........ *A61C 17/0202* (2013.01); *A61C 15/046* (2013.01); *A61C 17/08* (2019.05); *A61C 17/084* (2019.05); *A61C 17/092* (2019.05); *A61K 8/21* (2013.01); *A61Q 11/00* (2013.01)

(58) Field of Classification Search
CPC ....... A61C 17/06; A61C 17/08; A61C 17/092; A61C 15/046; A61C 15/047; A61C 15/048; A61C 17/0208
See application file for complete search history.

(56) References Cited

U.S. PATENT DOCUMENTS

| | | | | |
|---|---|---|---|---|
| 730,128 | A * | 6/1903 | Jordan | |
| 3,472,247 | A * | 10/1969 | Borsum | A61C 15/046 132/322 |
| 4,031,908 | A * | 6/1977 | Ting | A46B 11/063 132/322 |
| 5,183,064 | A * | 2/1993 | Barth | A61C 15/00 132/321 |
| 5,232,002 | A * | 8/1993 | McClallen | A61C 15/046 132/323 |
| 5,251,651 | A * | 10/1993 | Mason | A61C 15/046 132/324 |
| 6,309,218 | B1 * | 10/2001 | Ellenbecker | A61C 17/08 433/93 |
| 8,419,427 | B2 * | 4/2013 | Effenberger | A61C 15/00 433/136 |
| 9,375,299 | B2 * | 6/2016 | Syed | A61C 17/0202 |
| 2015/0059791 | A1 * | 3/2015 | Sheppel | A61C 15/046 132/200 |
| 2017/0216003 | A1 * | 8/2017 | Maycher | A61C 15/041 |
| 2018/0318055 | A1 * | 11/2018 | Lipp | A61C 19/063 |

* cited by examiner

*Primary Examiner* — Ralph A Lewis
(74) *Attorney, Agent, or Firm* — Manuel de la Cerra

(57) ABSTRACT

A dental device is disclosed for applying medicine to a patient's teeth. The device includes a handle having a distal end and a proximal end. The handle has a handle lumen extending from the distal end towards the proximal end. The handle also has a suction exit port that is fluidly connected to the handle lumen. A fork is connected to the handle at the distal end. The fork includes a fork base with at least two prongs, wherein each prong has a suction port that is fluidly connected to the handle lumen through a prong lumen. Floss is strung across the two prongs.

16 Claims, 4 Drawing Sheets

(Along A-A)

(Along A-A)

DENTAL DEVICE FOR APPLYING MEDICINE TO A PATIENT'S TOOTH

1.0 CROSS-REFERENCE TO RELATED APPLICATIONS

None

2.0 FIELD OF THE INVENTION

This invention relates to dental instruments, and more particularly to the application of topical dental medicaments.

3.0 BACKGROUND

Topical dental medicaments are currently administered via one of three methods. Some medicaments are applied to a dental tray or are poured into a dental tray, which the patient bites into, some are administered via syringe, and others are applied with the dentist's fingers while holding the patient's mouth open. U.S. Pat. No. 8,663,177 to Fogel discloses, for example, a system for the delivery of topical medicament comprising a reservoir and a glove lumen, wherein an operator still must apply the medicament using a digit of his or her hand. Even if the device makes it convenient for a dentist to have the medicament close at hand, the medicament must still be applied while the mouth is held open, and the burden is still on the dentist to apply the medicament to the right place and in the right amount. The invention of Fogel is not well adapted to applying medicament in the mouth, as there is no protection against spills, no consideration for illuminating the area inside the mouth where the dentist would apply the medicament, and no consideration given to how to keep the area dry from pooling saliva.

In the treatment of dental caries, commonly known as cavities, a class of medicament called dental varnishes requires topical application to the tooth affected. Silver nitrate, silver fluoride, fluoride varnish, and silver diamine fluoride (hereinafter SDF) may all be categorized as dental varnishes. When applied, the dental varnish requires a short period of time to dry and to set on the tooth, so that the varnish forms a barrier acting against tooth decay. Because the dental varnish wears away over time, it is often recommended that patients see the dentist periodically to have the varnish reapplied. SDF has recently risen to a promising role in stopping the progression of a cavity, having recently been approved by the US FDA.

SDF is, as of the time of this application, currently only sold by two companies in the US, and only sold to dentists. It is a thin liquid that a dentist can apply to teeth with cavities. Its primary purpose is to arrest the progress of dental caries (cavities), but it also has a secondary effect of relieving dental hypersensitivity. Despite the effectiveness it has demonstrated, a major disadvantage of SDF is that it will stain gums, lips, cheeks, clothing, and tabletops (basically any oxidizable surface) due to the oxidation of silver ions in SDF. The stain appears as a dark black lasting several days on skin and gums, so the dentist would have to be very careful in applying it only to teeth. Other side effects include pulpal irritation and oral soft tissue irritation, so the dentist applying SDF to a patient's teeth has even more motivation to not let this dental varnish touch any surface other than the tooth.

In current art, however, there are difficulties associated with applying SDF. To start, often times cavities start in between two teeth in the back of the mouth that are touching. There is no direct access to get a toothbrush in between the teeth. Fortunately, dental floss has become the commonly accepted 'carrier' of SDF in between the affected teeth. The process for the dentist is as follows: place cotton to isolate teeth as best as possible, place standard string floss between the patient's teeth, apply a drop of SDF to the end of the floss so it will wick across the hidden area where the cavities are, maintain the floss there for 30-60 seconds, and carefully remove everything from the patient's mouth without letting the SDF touch other parts of the mouth. Unfortunately, there is no device available that makes holding the floss easy, keeps the tongue and cheek tissues away from the teeth being treated, and removes pooling saliva simultaneously. Under the current art, the dentist has to get his or her fingers inside the patient's mouth, isolate to keep the area dry from saliva pooling, place the floss, apply the SDF with a small floss and then wait 30-60 seconds. This becomes very difficult and stressful for the dentist, especially considering that young children comprise the population on whom SDF is most commonly used to halt the progression of cavities.

Therefore, a need exists for a device to enable a dentist to quickly and easily apply the necessary medicine to the patient's tooth without causing discomfort or unsightly staining.

4.0 SUMMARY

The present invention provides an elegant solution to the needs described above and offers numerous additional benefits and advantages, as will be apparent to persons of skill in the art. A dental device is disclosed for applying medicine to a patient's teeth. The device includes a handle having a distal end and a proximal end. The handle has a handle lumen extending from the distal end towards the proximal end. The handle also has a suction exit port fluidly connected to the handle lumen. A fork is connected to the handle at the distal end. The fork includes a fork base with at least two prongs, wherein each prong has a suction port fluidly connected to the handle lumen through a prong lumen. Floss is strung across the two prongs.

The device may also include a medicine reservoir on either or both of the prongs. The medicine reservoir is constructed to allow medicine deposited therein to wick along the floss. The prongs may also have a protrusion constructed to separate the patient's oral tissue from the suction port, thus allowing for more effective suction. The prongs may also have two suction ports, each of which is fluidly connected to the handle lumen through a prong lumen.

The floss may be made of a wicking material, such that medicine can wick along the length of the floss. The floss may further be impregnated with a medicine to prevent cavities, such as silver diamine fluoride.

The handle lumen defines an axis, and the prongs may extend away from the fork base in a direction that is not parallel to the axis. The direction may be adjustable.

The device handle may have finger grips to permit more comfortable operation and manipulation of the device. The device may also have a light to illuminate the floss.

A method for using the disclosed device is also disclosed.

Additional aspects, alternatives and variations as would be apparent to persons of skill in the art are also disclosed herein and are specifically contemplated as included as part of the invention. The invention is set forth only in the claims as allowed by the patent office in this or related applications, and the following summary descriptions of certain examples are not in any way to limit, define or otherwise establish the scope of legal protection.

5.0 BRIEF DESCRIPTION OF THE DRAWINGS

The invention can be better understood with reference to the following figures. The components within the figures are not necessarily to scale, emphasis instead being placed on clearly illustrating example aspects of the invention. In the figures, like reference numerals designate corresponding parts throughout the different views and/or embodiments. Furthermore, various features of different disclosed embodiments can be combined to form additional embodiments, which are part of this disclosure. It will be understood that certain components and details may not appear in the figures to assist in more clearly describing the invention.

Figure 8:
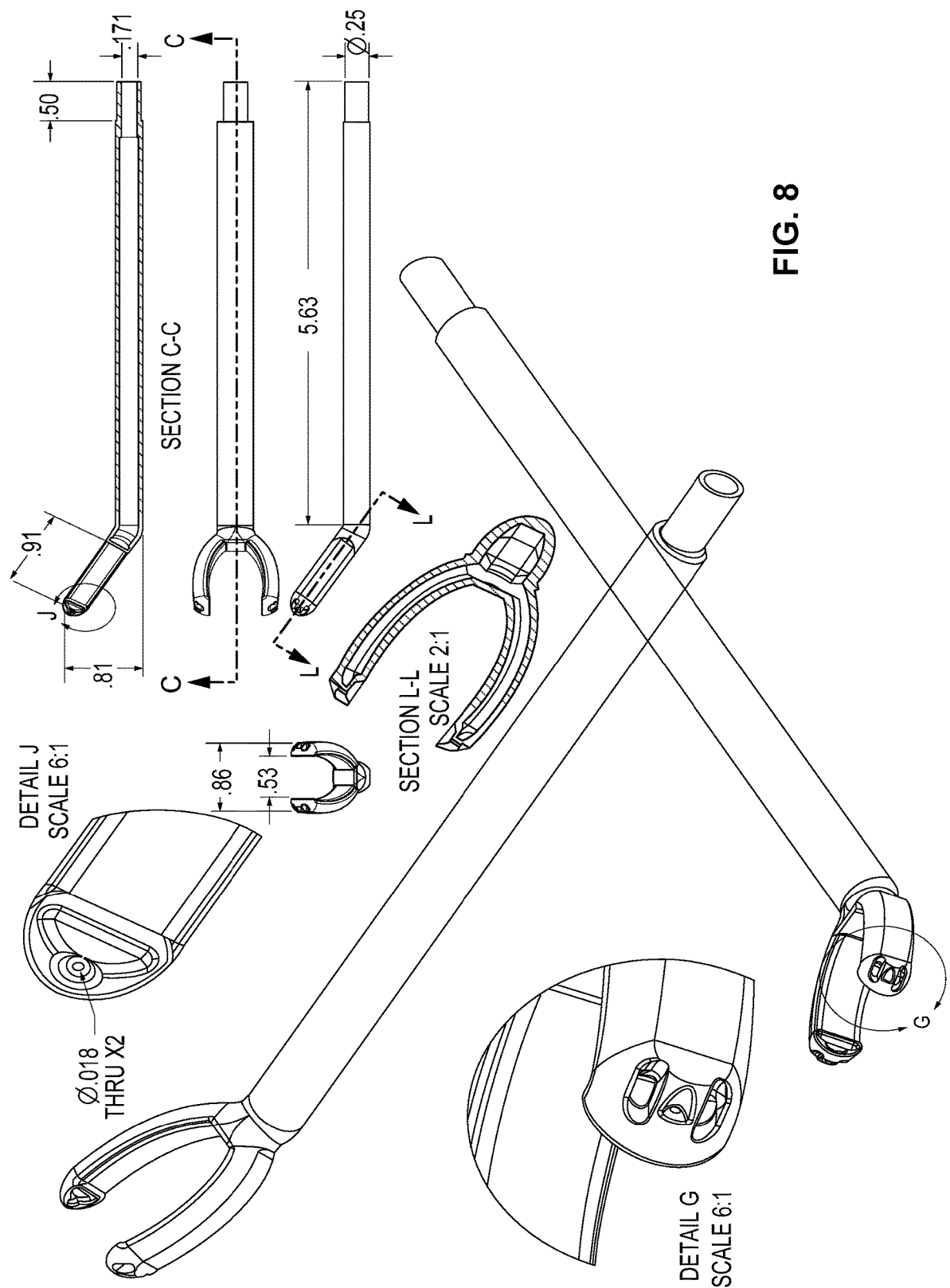

FIG. 8 provides various views and dimensions, in inches, of an embodiment of the dental device.

6.0 DETAILED DESCRIPTION

Reference is made herein to some specific examples of the present invention, including any best modes contemplated by the inventor for carrying out the invention. Examples of these specific embodiments are illustrated in the accompanying figures. While the invention is described in conjunction with these specific embodiments, it will be understood that it is not intended to limit the invention to the described or illustrated embodiments. To the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, process operations well known to persons of skill in the art have not been described in detail in order not to obscure unnecessarily the present invention. Various techniques and mechanisms of the present invention will sometimes be described in singular form for clarity. However, it should be noted that some embodiments include multiple iterations of a technique or multiple mechanisms unless noted otherwise. Similarly, various steps of the methods shown and described herein are not necessarily performed in the order indicated, or performed at all in certain embodiments. Accordingly, some implementations of the methods discussed herein may include more or fewer steps than those shown or described.

Further, the techniques and mechanisms of the present invention will sometimes describe a connection, relationship or communication between two or more entities. It should be noted that a connection or relationship between entities does not necessarily mean a direct, unimpeded connection, as a variety of other entities or processes may reside or occur between any two entities. Consequently, an indicated connection does not necessarily mean a direct, unimpeded connection unless otherwise noted.

The following list of example features corresponds with the attached figures and is provided for ease of reference, where like reference numerals designate corresponding features throughout the specification and figures:

Dental device 10
Proximal end 15
Distal end 20
Handle 25
Handle lumen 30
Suction exit port 35
Axis defined by handle lumen 40
Fork 45
Fork base 47
Prong(s) 50
Prong lumen 55
Suction ports 60
Prong direction 65
Angle 70
Floss 75
Floss anchor 80
Medicine reservoir 85
Suction flow path 90
Protrusion 95
Finger grips 100
Light 105
Suction device 110

Figure 1:
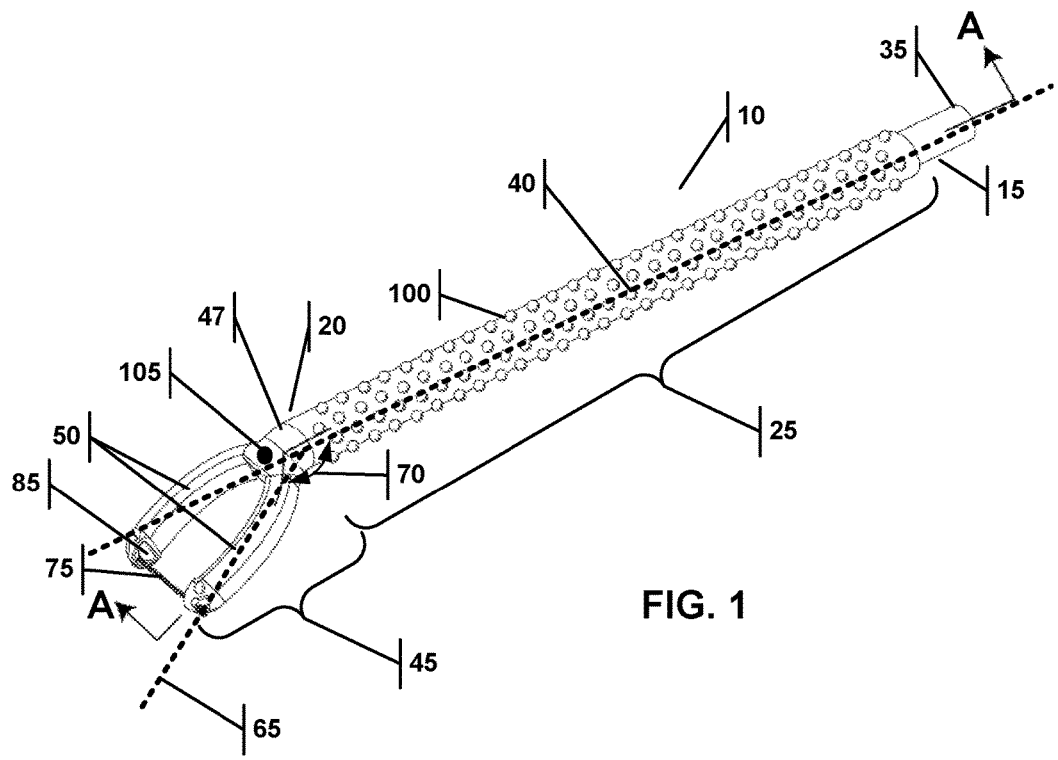
FIG. 1 is an isometric view of a novel dental device for applying medicine to a patient's teeth.

FIG. 1 presents the basic structure of the novel dental device of the present invention. The dental device 10 is comprised of a handle 25 portion as well as a fork 45 portion. The handle 25 has a distal end 20 and a proximal end 15. The distal end 20 connects to the fork 45 portion. The handle 25 features a handle lumen 30 (illustrated more clearly in FIGS. 3 and 4) that extends from the distal end 20 towards the proximal end 15, through which a fluid can flow (in other words, considered fluidly connected), and also features a suction exit port 35 connected to the handle lumen 30. While FIG. 1 illustrates the suction exit port 35 located at the proximal end 15, this need not be the case, as the suction exit port 35 can be located anywhere along the handle 25 without changing its purpose and function. The handle 25 extends along an axis 50 defined by the lumen 30 and can feature finger grips 100 located at the surface of the handle 25.

The fork 45 portion of the device 10 is comprised of a fork base 47 with the prongs 50 and a floss 75 strung across the prongs 50 in the fork base 47. The floss 75 can be comprised of a wicking material to wick the topical medicine from a reservoir to the tooth surface. The fork 45 has at least two prongs 50. Each prong 50 features a suction port 60 (shown more clearly in FIG. 2) that fluidly connects to the handle lumen 30 through a prong lumen 55. Also illustrated in FIG. 1 is an optional light 105 that is constructed in such a way as to illuminate the floss 75 and the area around which the operator of the device, presumably a dentist, would have to work, as well as a medicine reservoir 85 at the end of at least one prong 50 where the medicine deposited therein can wick along the floss 75. The dental device 10 may only have a medicine reservoir 85 on one of the prongs 50, or it may have a medicine reservoir 85 on more than one prong 50. The fork 45 portion may be constructed with more than two prongs 50, and the medicine reservoir 85 can be constructed on just one prong 50, or each prong 50. Medicine disposed of in the medicine reservoir 85 can wick along the floss 75.

The prongs 50 may extend away from the fork base 47 in a direction 65 that is not parallel to the axis 40 defined by the handle lumen 30, and may extend away from the axis 40 at an angle 70. This would be desirable because such an arrangement would not impede the operator/dentist's view of the floss site, as would happen were the prongs 50 extending parallel to the axis 40 of the handle 25 and handle lumen 30. Another advantageous variation that does not depart from the scope or spirit of this invention would be to enable the prongs 50 to extend away from the fork base 47 in a direction 65 that is adjustable. This would allow the operator of the dental device 10 more convenience, flexibility, comfort, and/or maneuverability. It would be well-known in the art to provide more than one way to adjust the direction 65, such as by constructing the prongs 50 and the prong lumens 55 out of a bendable material, constructing a hinge connection at the juncture of the fork base 47 with the handle 25, constructing a ball-and-socket joint type structure at the juncture of the fork base 47 with the handle 25, or any other method of adjusting the direction 65 known in the art.

Figure 2:
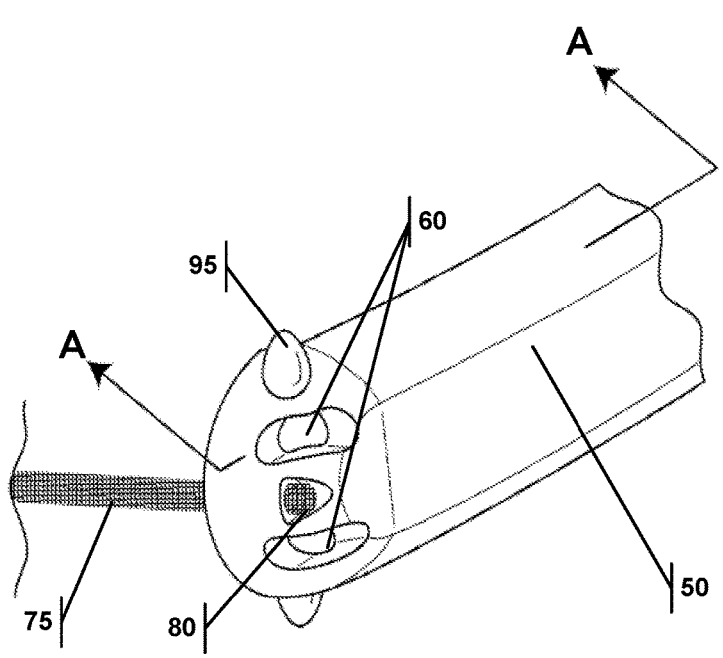
FIG. 2 is an enlarged view of a prong of the device of FIG. 1, view from the outside of the fork.
Figure 4:
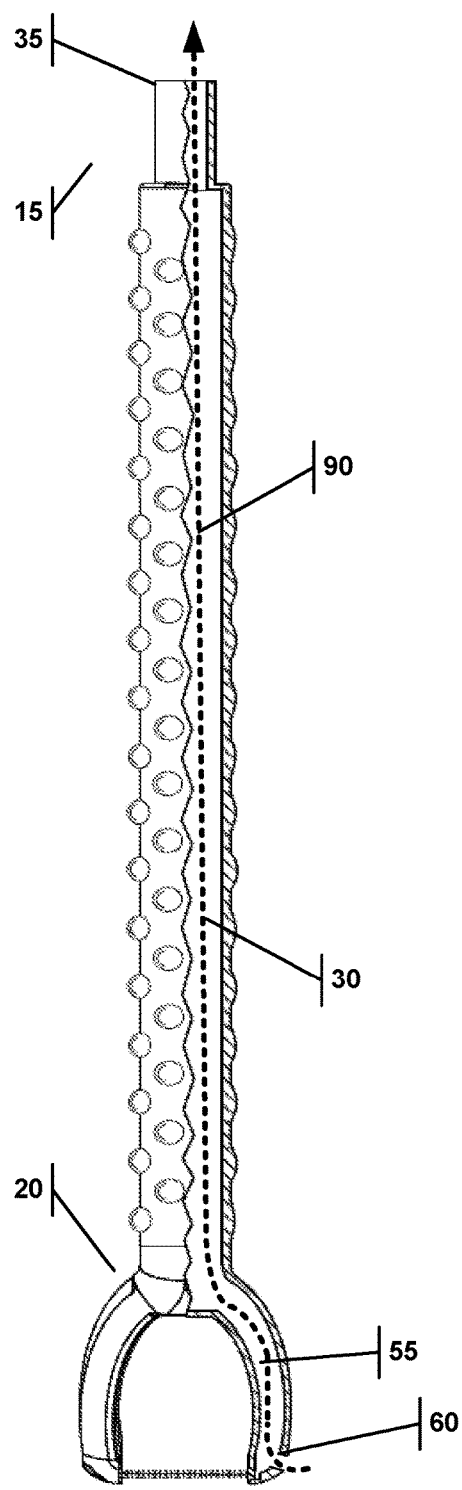
FIG. 4 is a partial cross-sectional view taken along line A-A from FIG. 1 to illustrate the handle lumen, prong lumen and suction flow path.
Figure 5:
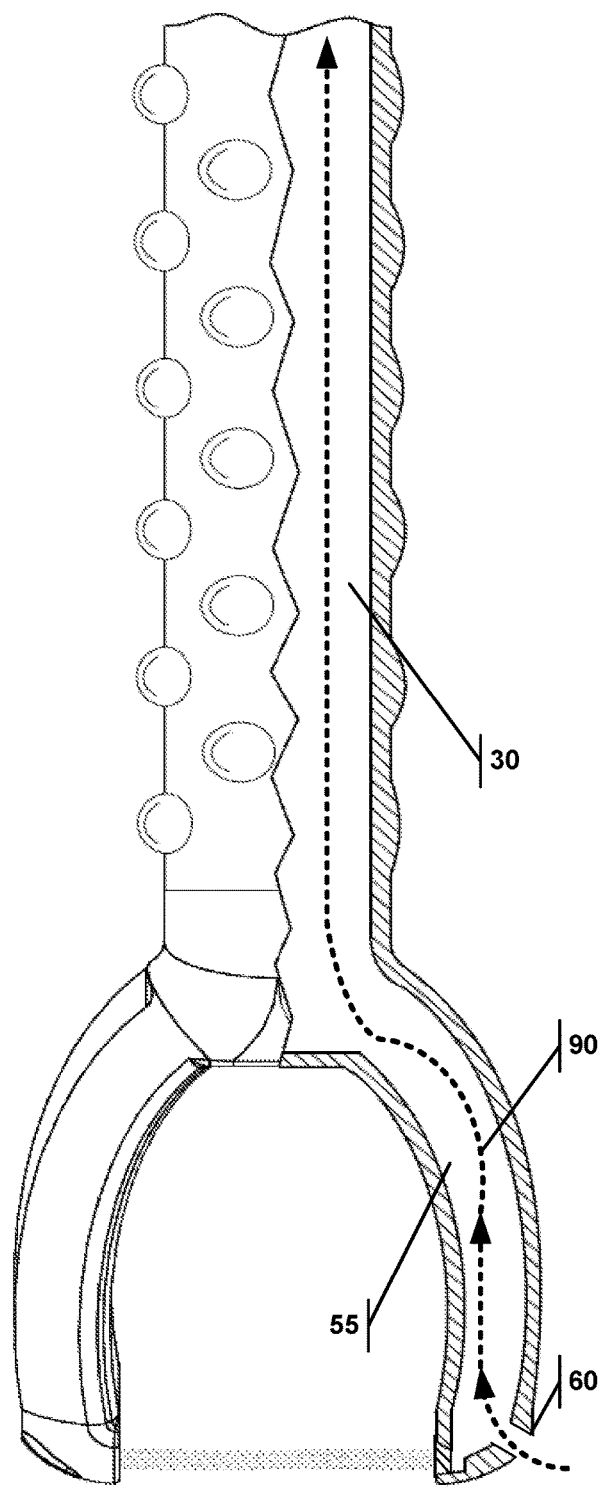
FIG. 5 is a partial cross-sectional enlarged view taken along line A-A from FIG. 1 to illustrate the handle lumen, prong lumen and suction flow path.

Referring now to FIG. 2, where an enlarged view of the end of a prong 50 is shown, the floss 75 is secured to a floss anchor 80 at the end of the prong 50. Each prong 50 can have one or more suction ports 60 to drain away the saliva that pools at the floss site through the suction port 60 through the prong lumen 55 to the handle lumen 30 and from there to the suction exit port 35, where the saliva can drain out, either through natural capillary action or, preferably, with the assistance of a suction device 110 (FIG. 6), which attaches to the suction exit port 35. Furthermore, the prongs 50 may comprise one or more protrusions 95 constructed to separate the patient's oral tissue from the suction port(s) 60 so as not to impede the draining of saliva at the floss site. To further facilitate the drainage of pooled saliva at the floss site, each prong 50 may for example have two suction ports 60 instead of just one such suction port 60. If each prong 50 has more than one suction port 60, each suction port 60 is fluidly connected to the handle lumen 30 through the prong lumen 55. The flow path of the drained saliva is illustrated in both FIGS. 4 and 5, which show the suction flow path 90 starting from the prong lumen 55 just after the saliva enters the suction port 60, going on through the handle lumen 30, until the saliva drains out of the device 10 at the suction exit port 35. Although FIG. 4 illustrates the suction exit port 35 as being located at the proximal end 15 of the dental device 10, the suction exit port 35 may be located anywhere along the handle 25 without departing from the spirit and scope of the present invention.

Figure 3:
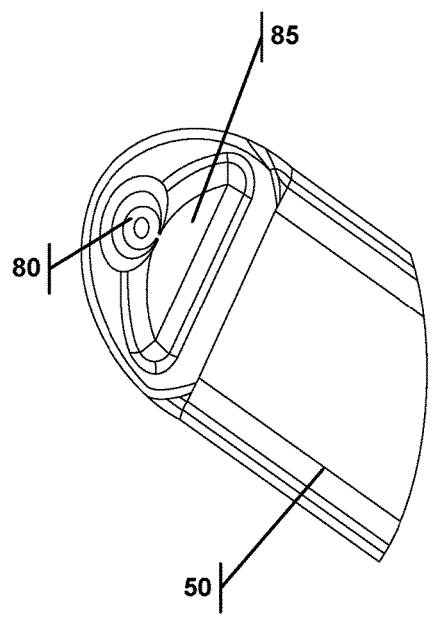
FIG. 3 is an enlarged view of a prong of the device of FIG. 1, view from the inside of the fork with the floss removed.

As FIG. 3 shows, the floss anchor 80 can be constructed in close proximity to the medicine reservoir 85, such that a floss 75 connected to the floss anchor 80 can wick medicine deposited into the medicine reservoir 85. The dental device 10 can be designed for reuse or for one-time use. The dental device 10 can also be designed without the medicine reservoir 85, such as if the medicine were incorporated into the floss 75 itself. The floss 75 may comprise a medicine to prevent cavities, such as a dental varnish. Furthermore, the floss 75 may comprise silver diamine fluoride (SDF), which is one type of dental varnish. The dental device 10 may also be adapted for applying a broader class of topical dental medicaments.

To use the dental device 10 to apply medicine to a patient's tooth, a dentist would employ the method that follows. First, suction is applied to the suction exit port 35. In the second step, the floss 75 is inserted between a first set of teeth (illustrated in FIG. 6). Third, medicine is applied to the floss 75. Next, the dentist may leave the floss 75 between the first set of teeth for a predetermined period of time. Finally, the dental device 10 may be removed by the dentist from the patient's mouth.

When the dental device comprises a medicine reservoir 85 on at least one of the prongs 50, and the medicine reservoir 85 is constructed to allow medicine deposited therein to wick along the floss 75, the third step just comprises applying medicine to the medicine reservoir 85. As stated previously, the medicine used on the floss 75 may comprise a medicant used for treatment of cavities, including the arrest of dental caries, or cavities. The predetermined period that the dental device 10 is left inside the patient's mouth, in the fourth step, may be between 30 and 60 seconds, as is typical when a topical dental varnish is the medicine applied. The medicine applied may also be silver diamine fluoride.

The same dental device 10 may be used by the dentist for more than one set of teeth during the same patient visit. If using on more than one set of teeth, the dentist would additionally perform the steps of: removing the floss 75 from between the first set of teeth, inserting the floss 75 between a second set of teeth, and leaving the floss 75 between the second set of teeth for a predetermined period of time. Depending on how much medicine is left on the floss 75 or in the medicine reservoir 85 between applying the medicine to the first set of teeth and to the second set of teeth, the dentist may optionally also perform the step of applying medicine to the floss 75 after inserting the floss 75 between a second set of teeth. In some cases where more than two sets of teeth require the application of medicine, these steps could be repeated for a third set of teeth, fourth set of teeth, and so forth.

Figure 6:
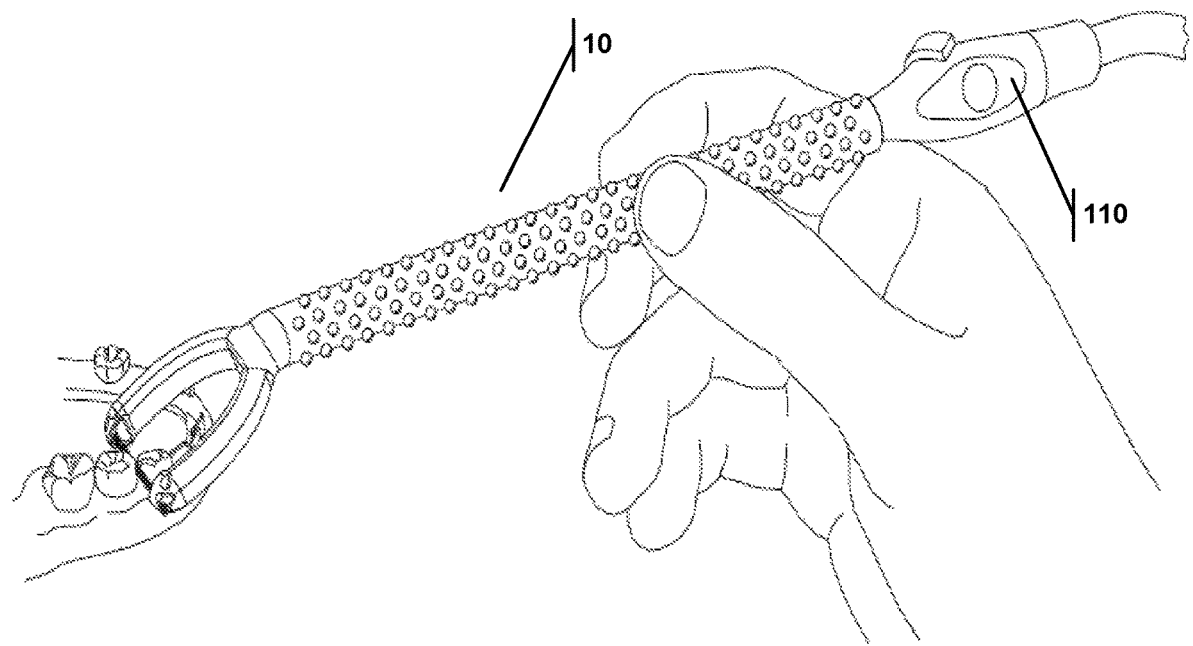
FIG. 6 illustrates the dental device connected to a suction device, and is intended to show the application of medicine to a patient's teeth using the device.
Figure 7:
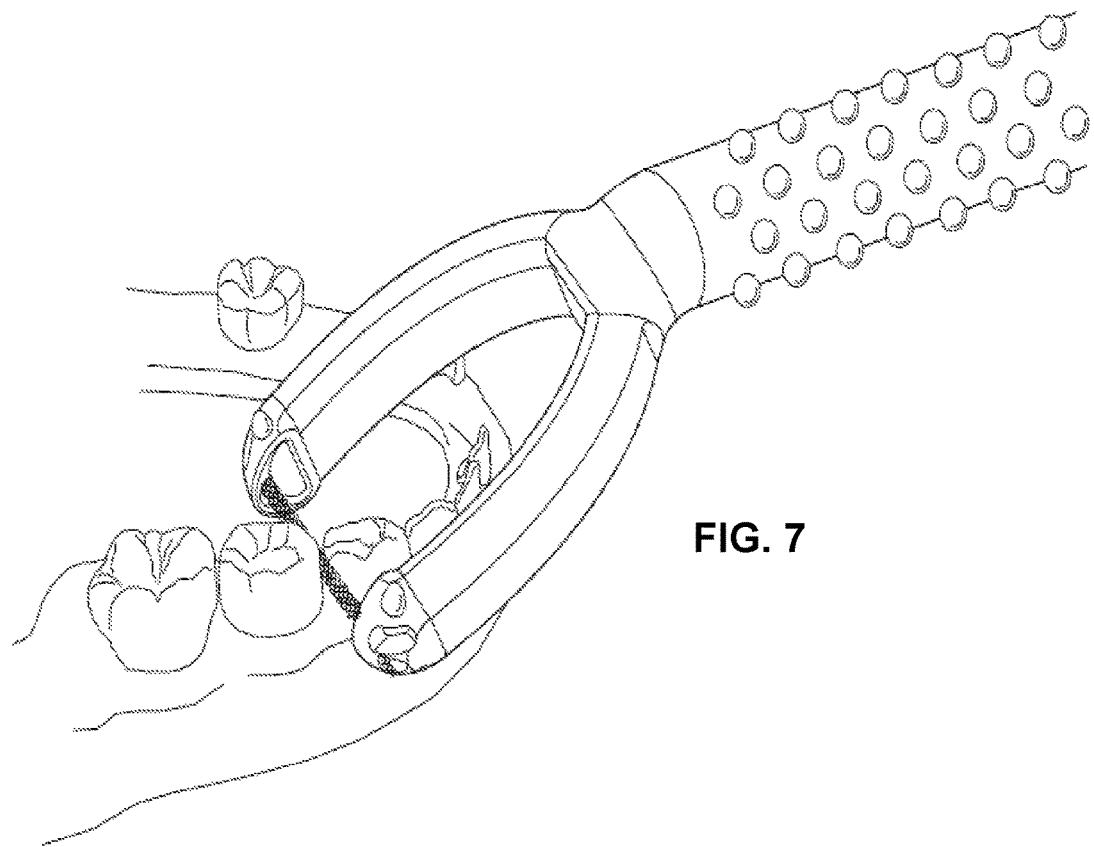
FIG. 7 is an enlarged view illustrating the application of medicine using the device.

The advantages of the dental device 10 of the present invention are numerous. Compared to the current art of having the dentist simultaneously trying to keep the patient's mouth open, trying to operate a floss to apply a topical medicament such as silver diamine fluoride without contacting and staining other surfaces, and trying to isolate the set of teeth or floss site such that saliva does not pool in order to ensure the medicament sets on or in the teeth, using the dental device 10 accomplishes these objectives more simply, with more convenience and less stress to both the patient and the dentist. As illustrated in FIGS. 6-7, the dentist need not place his or her hand inside the patient's mouth, and only the fork 45 portion of the dental device 10 need be inside the patient's mouth. The floss 75 would automatically dispense the medicine, which is either incorporated into the floss 75 itself, or can be wicked from a medicine reservoir 85 built into the prong(s) 50. The patient need only keep his or her mouth open wide enough for the fork 45 instead of wide enough for the dentist's entire hand to fit into his or her mouth. The dentist need only operate the handle 25 and connect the suction device 110, if using, to the exit suction port 35, and occasionally fill up the medicine reservoir 85, if applicable. This saves both the patient and the dentist time, as the dentist would be able to see the floss site more clearly with the help of the optional light 105, instead of feeling around and applying medicine in the blind while his or her hand is inside the patient's mouth. Because the novel dental device 10 of the present invention enables the dentist to apply medicine with accuracy while simultaneously isolating the patient's tongue and cheeks from the application site of the medicine, there is much less risk of staining or causing spillage and irritation of the patient's soft tissues within and without the mouth. The novel dental device 10 of the present invention saves both dentist and patient time and stress.

The various views of FIG. 8 provide measurements and ratios of the various components of the dental device 10. They are provided as references to give more details of one particular possible embodiment, and are not meant in any way to limit either the scope or spirit of this invention.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently-preferred embodiment of the invention and are therefore representative of the subject matter which is broadly contemplated by the present invention. It is further understood that the scope of the present invention fully encompasses other embodiments that may become obvious to those skilled in the art, and that the scope of the present invention is accordingly limited by nothing other than the appended claims.

The invention claimed is:

1. A dental device for applying medicine to a patient's tooth, the device comprising:
   a handle having a distal end and a proximal end, the handle comprising:
      a handle lumen extending from the distal end towards the proximal end;
      a suction exit port fluidly connected to the handle lumen; and
   a fork connected to the handle at the distal end, the fork comprising:
      a fork base with at least two prongs, wherein each prong has a suction port fluidly connected to the handle lumen through a prong lumen;
      floss strung across the two prongs; and
      a medicine reservoir on at least one of the prongs, the medicine reservoir constructed to allow medicine deposited therein to wick along the floss.

2. The dental device of claim 1, wherein the handle lumen defines an axis, and wherein the prongs extend away from the fork base in a direction that is not parallel to the axis.

3. The dental device of claim 1, wherein the prongs extend away from the fork base in a direction that is adjustable.

4. The dental device of claim 1, further comprising a protrusion constructed to separate the patient's oral tissue from the suction port.

5. The dental device of claim 1, wherein the handle comprises finger grips.

6. The dental device of claim 1, wherein the floss is comprised of a wicking material.

7. The dental device of claim 1, wherein each prong has two suction ports, each of which is fluidly connected to the handle lumen through the prong lumen.

8. The dental device of claim 1, further comprising a light constructed to illuminate the floss.

9. The dental device of claim 1, wherein the floss comprises a medicine to prevent cavities.

10. The dental device of claim 1, wherein the floss comprises silver diamine fluoride.

11. A method of applying medicine to a patient's tooth using the device of claim 1, the method comprising:
   a. applying suction to the suction exit port;
   b. inserting the floss between a first set of teeth;
   c. applying medicine to the floss and to the medicine reservoir;
   d. leaving the floss between the first set of teeth for a predetermined period of time; and
   e. removing the device from the patient's mouth.

12. The method of claim 11, wherein the predetermined period of time is 30 to 60 seconds.

13. The method of claim 11, wherein the medicine comprises a medicine to arrest the progression of cavities.

14. The method of claim 11, wherein the medicine comprises silver diamine fluoride.

15. The method of claim 11, further comprising after step (d):
   d1. removing the floss from between the first set of teeth
   d2. inserting the floss between a second set of teeth; and
   d3. leaving the floss between the second set of teeth for a predetermined period of time.

16. The method of claim 15, further comprising applying medicine to the floss after step d2.

* * * * *